United States Patent
Khandoker

(10) Patent No.: US 11,185,275 B2
(45) Date of Patent: Nov. 30, 2021

(54) LOW COST FETAL PHONOCARDIOGRAM

(71) Applicant: Khalifa University of Science and Technology, Abu Dhabi (AE)

(72) Inventor: Ahsan Khandoker, Abu Dhabi (AE)

(73) Assignee: Khalifa Univeristy of Science and Technology, Abu Dhabi (AE)

( * ) Notice: Subject to any disclaimer, the term of this patent is extended or adjusted under 35 U.S.C. 154(b) by 275 days.

(21) Appl. No.: 15/756,822

(22) PCT Filed: Sep. 2, 2016

(86) PCT No.: PCT/IB2016/055284
§ 371 (c)(1),
(2) Date: Mar. 1, 2018

(87) PCT Pub. No.: WO2017/037678
PCT Pub. Date: Mar. 9, 2017

(65) Prior Publication Data
US 2018/0256057 A1    Sep. 13, 2018

Related U.S. Application Data

(60) Provisional application No. 62/213,500, filed on Sep. 2, 2015.

(51) Int. Cl.
*A61B 5/024* (2006.01)
*A61B 5/344* (2021.01)
(Continued)

(52) U.S. Cl.
CPC .......... *A61B 5/344* (2021.01); *A61B 5/02411* (2013.01); *A61B 5/6831* (2013.01);
(Continued)

(58) Field of Classification Search
CPC ..... A61B 5/0011; A61B 5/0205; A61B 5/024; A61B 5/02411; A61B 5/02438;
(Continued)

(56) References Cited

U.S. PATENT DOCUMENTS 3,409,737 A * 11/1968 Settler ................ A61B 5/02411
600/528
4,781,200 A * 11/1988 Baker ................ A61B 5/02411
600/483
(Continued)

FOREIGN PATENT DOCUMENTS

WO    2015063520 A1    5/2015
WO    2017037678 A1    3/2017

OTHER PUBLICATIONS

A. Jimenez-Gonzalez and C. J. James, "Source separation of Foetal Heart Sounds and maternal activity from single-channel phonograms: A temporal independent component analysis approach," 2008 Computers in Cardiology, Bologna, 2008, pp. 949-952, doi: 10.1109/CIC.2008.4749200.*

(Continued)

*Primary Examiner* — Eugene T Wu
(74) *Attorney, Agent, or Firm* — Kilpatrick Townsend & Stockton LLP

(57) ABSTRACT

A fetal phonocardiogram system featuring an array of acoustic sensors designed to be temporarily affixed to a pregnant patient to convert the vibrations associated with a fetal heartbeat and/or fetal movement into a signal. The signal can be amplified and transferred to a processing element for filtering non-fetal sounds in order to resolve the fetal heartbeat. The filtered signal can be used in conjunction with an array of multiple acoustic sensors to locate a fetal position relative to the array.

12 Claims, 10 Drawing Sheets

(51) Int. Cl.
*A61B 5/00* (2006.01)
*A61B 8/02* (2006.01)
*A61B 8/08* (2006.01)
*A61B 7/04* (2006.01)
*A61B 7/00* (2006.01)
*A61B 5/11* (2006.01)

(52) U.S. Cl.
CPC .............. *A61B 5/7225* (2013.01); *A61B 7/00* (2013.01); *A61B 7/04* (2013.01); *A61B 8/02* (2013.01); *A61B 8/0866* (2013.01); *A61B 5/11* (2013.01); *A61B 2562/0204* (2013.01); *A61B 2562/04* (2013.01)

(58) Field of Classification Search
CPC ..... A61B 5/02444; A61B 5/0444; A61B 5/11; A61B 5/4362; A61B 5/6801; A61B 5/6802; A61B 5/6804; A61B 5/6823; A61B 5/683; A61B 5/6831; A61B 5/6835; A61B 5/7203; A61B 5/7207; A61B 5/721; A61B 5/7214; A61B 2503/02; A61B 2562/04; A61B 2562/046; A61B 2562/06; A61B 2562/066
See application file for complete search history.

(56) References Cited

U.S. PATENT DOCUMENTS

| | | | | |
|---|---|---|---|---|
| 5,817,035 | A * | 10/1998 | Sullivan | A61B 5/4362 600/588 |
| 6,171,263 | B1 | 1/2001 | Sullivan | |
| 2007/0260155 | A1* | 11/2007 | Rapoport | A61B 5/0444 600/528 |
| 2010/0022888 | A1* | 1/2010 | George | A61B 8/02 600/459 |
| 2010/0256529 | A1* | 10/2010 | Grasing | A61B 7/04 600/586 |
| 2014/0249436 | A1 | 9/2014 | Kabakov et al. | |
| 2016/0270670 | A1* | 9/2016 | Oz | A61B 5/0245 |

OTHER PUBLICATIONS

M. Samieinasab and R. Sameni, "Fetal phonocardiogram extraction using single channel blind source separation," 2015 23rd Iranian Conference on Electrical Engineering, Tehran, 2015, pp. 78-83, doi: 10.1109/IranianCEE.2015.7146186.*
PCT/IB2016/055284, "International Search Report and Written Opinion", dated Dec. 7, 2016, 17 pages.
PCT/IB2016/055284, "International Preliminary Report on Patentability", dated Mar. 15, 2018, 14 pages.

* cited by examiner

LOW COST FETAL PHONOCARDIOGRAM

CROSS-REFERENCE TO RELATED APPLICATIONS

This application is a U.S. 371 of International Application No. PCT/IB16/55284, filed on Sep. 2, 2016, which application claims the benefit of U.S. Provisional Application No. 62/213,500 filed Sep. 2, 2015, the entire contents of which are hereby incorporated for all purposes in their entirety.

BACKGROUND

Changes in the fetal heart rate such as reduced variability or episodes of slowing and reductions in fetal movements can be useful indicators of reduced fetal well-being, and thus the need for obstetric interventions. These physiological parameters need to be measured over a long period on the order of minutes to be useful. Current methods of assessment are either too brief (e.g., manual counting using a fetal stethoscope) or else require expensive equipment and a skilled operator (e.g., cardiotocography (CTG) and Doppler ultrasound). There are also concerns about the safety of prolonged exposure to ultrasound.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

A fetal phonocardiogram system can include one or more phonocardiogram sensors, which may each have a casing, an acoustic chamber protruding from the casing, and a sensor or acoustic transducer connected with the acoustic chamber and configured to convert acoustic waves into a signal. In some cases the sensor can be a piezoelectric transducer. A fetal phonocardiogram system can further include a conditioning element or elements for amplifying signals from the one or more sensors, which can include one or more signal conditioning circuits. However, in some cases, signal conditioning may be accomplished at a circuit integrally assembled with the sensor. A fetal phonocardiogram system can also include a processing unit for receiving the amplified signals, performing one or more filtering steps based on environmental sounds, determining information concerning a fetal heartbeat from the signals, and causing information concerning the fetal heartbeat to be output in a manner detectable by a user. In some cases, the information can include the heart rate, the sound of the heartbeat, the acoustic intensity of the heartbeat from one or more locations, and the position of the fetus based on the position of the heartbeat.

A method for performing a fetal phonocardiogram can include receiving one or more signals from one or more acoustic transducers attached with a pregnant patient in proximity to an abdominal region of the patient, amplifying the signal or signals, modifying the signal or signals by removing signal frequencies not associated with a fetal heartrate to generate an output signal, and determining, from the output signal or signals, one or more of a fetal heart rate, the sound of the heartbeat, or the acoustic intensity of the heartbeat from one or more locations. By utilizing multiple acoustic transducers in an array, acoustic intensities of the fetal heartbeat from multiple positions can be obtained in conjunction with the associated positions, permitting a user to obtain the position of the fetus based on the fetal heartbeat. Additional information can be obtained by configuring the sensors to detect different frequency ranges: for example, fetal movement can be detected by one or more acoustic transducers configured to detect low-frequency vibration.

For a filler understanding of the nature and advantages of the present invention, reference should be made to the ensuing detailed description and accompanying drawings.

BRIEF DESCRIPTION OF THE DRAWINGS

These and other features, embodiments, and advantages of the present disclosure are better understood when the following Detailed. Description is read with reference to the accompanying drawings.

DETAILED DESCRIPTION

Figure 1:
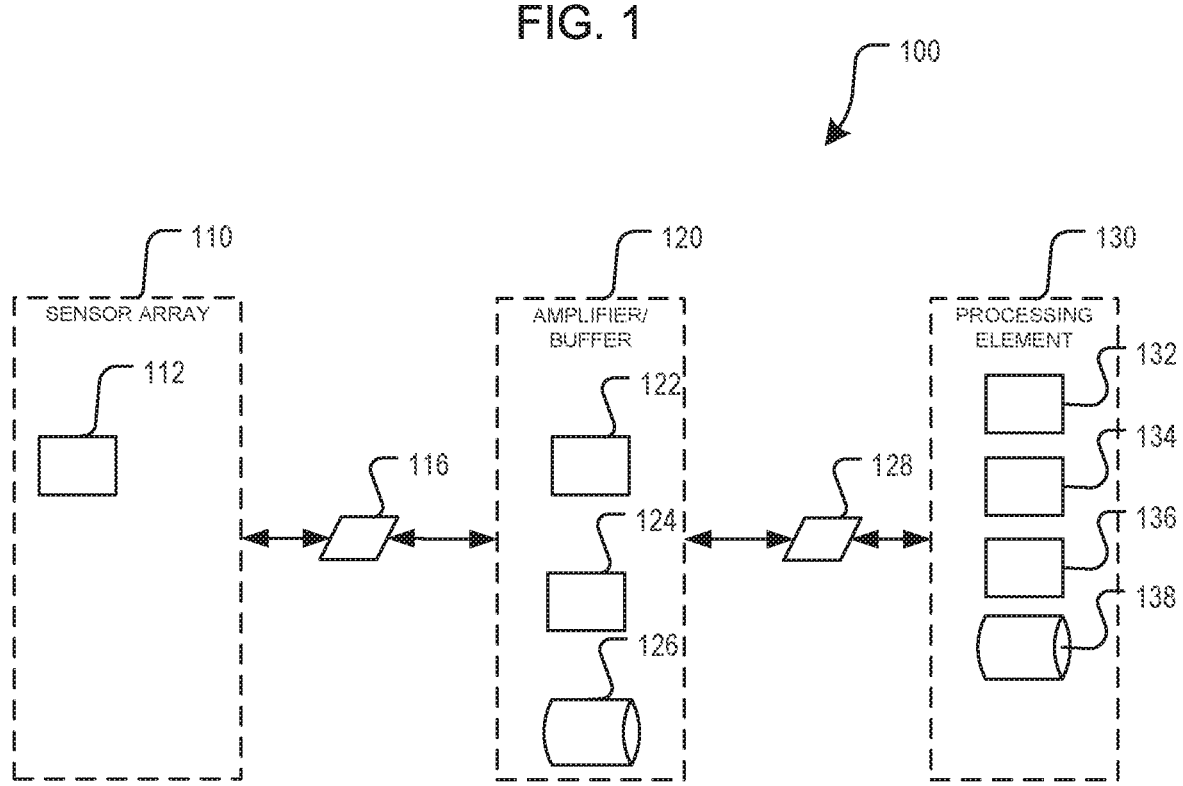
FIG. 1 is a block diagram illustrating a first example of a fetal phonocardiogram system, in accordance with embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Various embodiments herein described are directed to systems and methods for obtaining and processing abdominal phonographic data during pregnancy for assessing fetal health and/or determining a need for obstetric intervention. In some embodiments, a system for obtaining said phonographic data may include one or more sensors, an amplifier, and a processing unit for processing the phonographic data and providing information to a user. In some cases, a sensor can include an acoustic transducer which can be applied to a patient's abdomen and used to sense sound waves within the patient corresponding to a fetal heartbeat, fetal movement, and various endogenous sounds corresponding to the patient and unrelated to the fetus. By employing acoustic transducers, the system can use inexpensive component parts such as piezoelectric disk transducers (or other suitable low-cost microphones), reducing an overall cost of providing fetal monitoring.

In embodiments, an array of multiple sensors may be arranged in a predetermined spacing such that at least one sensor will be located sufficiently close to the fetus to detect a heartbeat of the fetus even if the array is applied without prior knowledge of the location of the fetus. The predetermined spacing may be achieved by attaching the sensors with a support structure, and either the sensors or the support structure can also be attached with one or more straps or belts for attaching the array to a patient. An array incorporating a predefined spacing and a support structure may be readily applied to a patient even by an inexperienced practitioner, or by the patient herself, further reducing costs associated with fetal monitoring.

In some cases, one or more of the sensors in either of the above-described systems may include onboard memory or a buffer to store sound data, but in other cases; sound data may be transmitted continuously to an amplifier, external buffer; or external processing unit. In specific embodiments, a combined signal conditioning element can be configured to collect a stream of acoustic data from the array of sensors, perform initial processing (e.g., amplification and/or frequency filtering) on the acoustic signals, and store the processed signals in a buffer. The signal conditioning element can push the processed signals to a processing element for performing analysis on the signals and displaying results to a user, or the processing element can retrieve the processed signals.

In some cases, one or more of the sensors in a sensor array can be configured for detecting frequencies in a different range than the other sensors. For example, very low frequency ranges (approximately 0.5-2 Hz), being commonly associated with fetal body and limb movements, can be targeted for detection by one or more of the sensors. Typical fetal heart sounds are commonly associated with a higher frequency range (approximately 20-150 Hz), and can be detected concomitantly by other sensors in the array.

In embodiments, filtering acoustic signals from an array of sensors can include multiple aspects for distinguishing fetal heartrate from interference. Interference may originate from endogenous sounds of the patient such as speech, digestive activity, maternal pulse, heartbeat and respiratory sounds, and shear sources caused by movements of the acoustic sensor against the skin of the patient. Due to the acoustic damping of the amniotic fluid and maternal tissue, amplification is needed to hear the desired fetal sounds; and amplification can also increase the impact of interference. A first aspect of filtering acoustic signals can include selecting frequencies by using low-pass and high-pass filtering at the signal conditioning element and/or at the individual sensors in order to remove frequencies not associated with fetal heartbeat and movement. A second aspect of filtering acoustic signals can include processing to cancel undesired sounds. For example, the maternal heartbeat, being a regular sound readily detected at all sensors in an array (and also readily detected by other means) can be captured and placed out of phase with the acoustic signals received from the array of sensors in order to selectively cancel the maternal heartbeat from a processed acoustic signal. By way of further example, using a blind source separation method using a wavelet transform, mixed signals (i.e., from the mother, fetus, and external environment) can be captured and separated into independent acoustic waveforms. The waveform associated with the fetus can be extracted from the mixed acoustic signals in this way and analyzed independently.

In embodiments, the system can incorporate buffering at an signal conditioning element for managing a flow of acoustic data. In some cases, the acoustic data can be provided via a simple connector, such as a standard audio port having first and second stereo pin leads, and a microphone lead. By managing acoustic data via a buffer, the data can be transferred to a highly portable device, such as a mobile phone, tablet, or other small electronic computing device, via a standard audio cable. The portable device can also provide processing functionality for analyzing the acoustic signals and outputting information to a user; and executable instructions for performing the processing can be pre-loaded on the device, operated via cloud computing on a device with an active network connection, or can be installed to the device via a network, such as a wireless network.

Referring now to the drawings, in which like reference numerals represent like parts throughout the several views, FIG. 1 shows a block diagram illustrating a fetal phonocardiogram system 100, in accordance with embodiments. The system 100 includes a sensor array 110, an signal conditioner element 120 and a processing element 130. The sensor array 100 can include at least one sensor 112 (or an arrangement of multiple sensors) which connects, e.g., via wires, with the signal conditioner element 120. The sensor 112 transfers raw acoustic data 116 to the signal conditioner element 120, which can include a data I/O module 122, a first signal processing module 124, and a first buffer 126 which can include one or more memory elements for storing an acoustic signal digitally. In some cases, the signal conditioning element 120 can also communicate with the sensor 112, for example, to turn sensors off or on, to adjust a gain at a sensor having onboard sensitivity control, or any other suitable function. The signal conditioner element 120 can send amplified acoustic data 128 to the processing element 130, which in some cases may be a mobile device, such as a smartphone or tablet having one or more processors and memory storing executable instructions. The processing element 128 can include a second data I/O module 132, a second signal processing module 134, a user I/O module 136 for enabling the processing element 130 to be controlled by a user, and a second buffer 138 for storing amplified signals obtained from the signal conditioner element 120 and for storing processed signals generated at the processing element 130.

Figure 2:
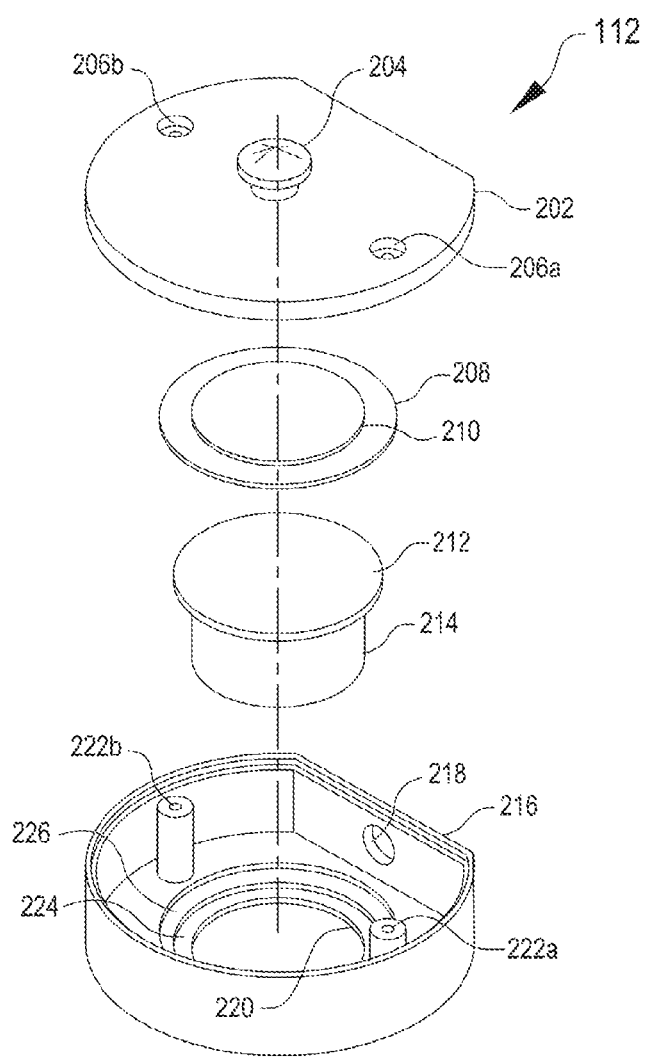
FIG. 2 is an exploded perspective view of a fetal phonocardiogram sensor, in accordance with embodiments.

FIG. 2 is an exploded perspective view of a fetal phonocardiogram sensor 112, suitable for use in a fetal phonocardiogram system such as the system 100 shown in FIG. 1, in accordance with embodiments. The sensor 112 includes a casing 216 which is attachable with a top cover 202 by way of attachment features 222a, 222b, 206a, and 206b, which can accommodate a bolt, screw, rivet, adhesive, or any other suitable means of fixedly attaching mechanical parts. In some specific embodiments, the top cover 202 and casing 116 can be connected with two M2™ flathead screws. The casing further includes a port 218 for accommodating electronic connectors, and a void 220 for accommodating an acoustic probe 214. The void 220 can be encompassed in first and second depressions 224 and 226 for securing the positions of the acoustic probe 214 and a sensor disk 208. When assembled, the acoustic probe 214 rests in the casing void 220, with a flanged end 212 facing upward and abutting the sensor disk 208 which has the sensor 210 thereon. Electronic connectors (not shown) can be connected with the sensor 210 and pass out of the casing 216 via the port 218. In some embodiments, the sensor disk 208 causes an electrical potential to occur across a portion of the sensor disk in response to physical excitation, such as acoustic vibrations or bending (as in a piezoelectric sensor disk), in which case electrical connectors can be used to transmit a signal generated by the sensor. In alternative embodiments, the sensor disk 208 may be an optical transducer, and may transmit a signal via optical fiber to an optical/electrical converter. Said alternative embodiments may be useful for cases where a patient may undergo a procedure that requires metals to be removed from the vicinity, such as MRI in conjunction with fetal monitoring.

In some embodiments of the sensor 112, the sensor disk 208 is a piezoelectric disk. In some specific embodiments, the sensor disk 208 can be a prefabricated (off-the-shelf) piezoelectric sensor disk having approximately the following attributes: a diameter of 15 mm, thickness of 0.3 mm, capacitance of 30 nF, and a resonance frequency of 2.8 kHz. Notably, off-the-shelf disk-type piezoelectric sensor disks are readily obtainable at low cost, enabling sensors such as the sensor 112 to be constructed at low cost as well. The casing 216 and the probe 214 can be formed of any suitable rigid plastic, metal, or comparable structural material by casting, 3D printing, or other suitable manufacturing technique. In some specific embodiments, the casing 116 and probe 214 can be formed of ABS plastic by either a fused deposition modeling (FDM) or a stereolithography (SLA) 3D-printing technique. In other cases, the casing 116 and probe 214 can be formed by conventional mass-production techniques such as injection molding or any other suitable production technique.

The top of the sensor top cover 202 can also include an attachment feature 204 for connecting the sensor 112 with a support structure (not shown) or a belt, strap, or other means of attaching the sensor with a patient (not shown). The attachment feature 204 can be a button-like protrusion, and can be fixedly attached with the cover 202, or with any part of an exterior surface of the sensor casing 216. In some specific embodiments, the attachment feature 204 is configured to be inserted, in the manner of a button, through a hole in a flexible support structure (not shown); but in other cases, the attachment feature can be a snap, threaded interface, magnetic connector, or any other suitable means for removably connecting two components.

Figure 3:
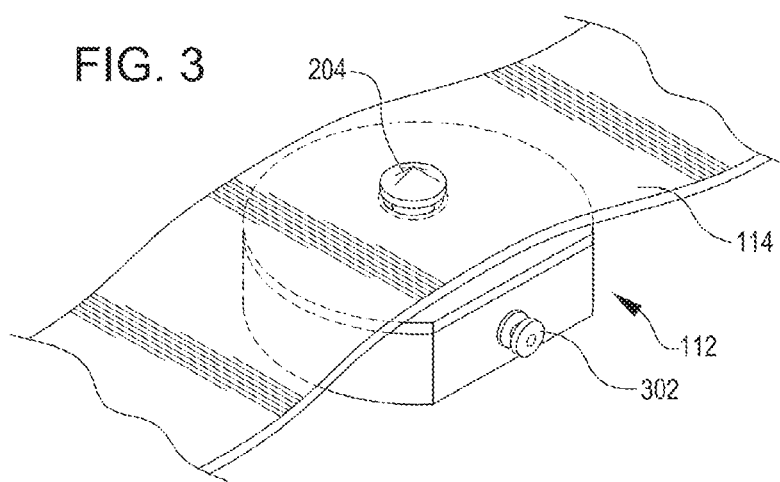
FIG. 3 is perspective view of a fetal phonocardiogram sensor and strap, in accordance with embodiments.

FIG. 3 is perspective view of a fetal phonocardiogram sensor 112 and strap 114, suitable for use in a fetal phonocardiogram system such as the system 100 shown in FIG. 1, in accordance with embodiments. In this view, the attachment feature 204 of the sensor 112 protrudes through the strap 114. The strap 114 can be a portion of a flexible support structure configured to align multiple sensors in a predetermined arrangement; or the strap 114 can be a portion of a belt arranged to pass around the body of a patient. In such cases, the strap 114 can include connecting features (not shown) such as snaps, buttons, Velcro® fastener, or other suitable means for connecting the strap 114 and sensor 112 to the patient. Notably, the strap 114 does not impinge on an audio port 302 protruding from the sensor 112 for connecting the sensor with an amplifier and/or signal conditioning system.

Figure 4:
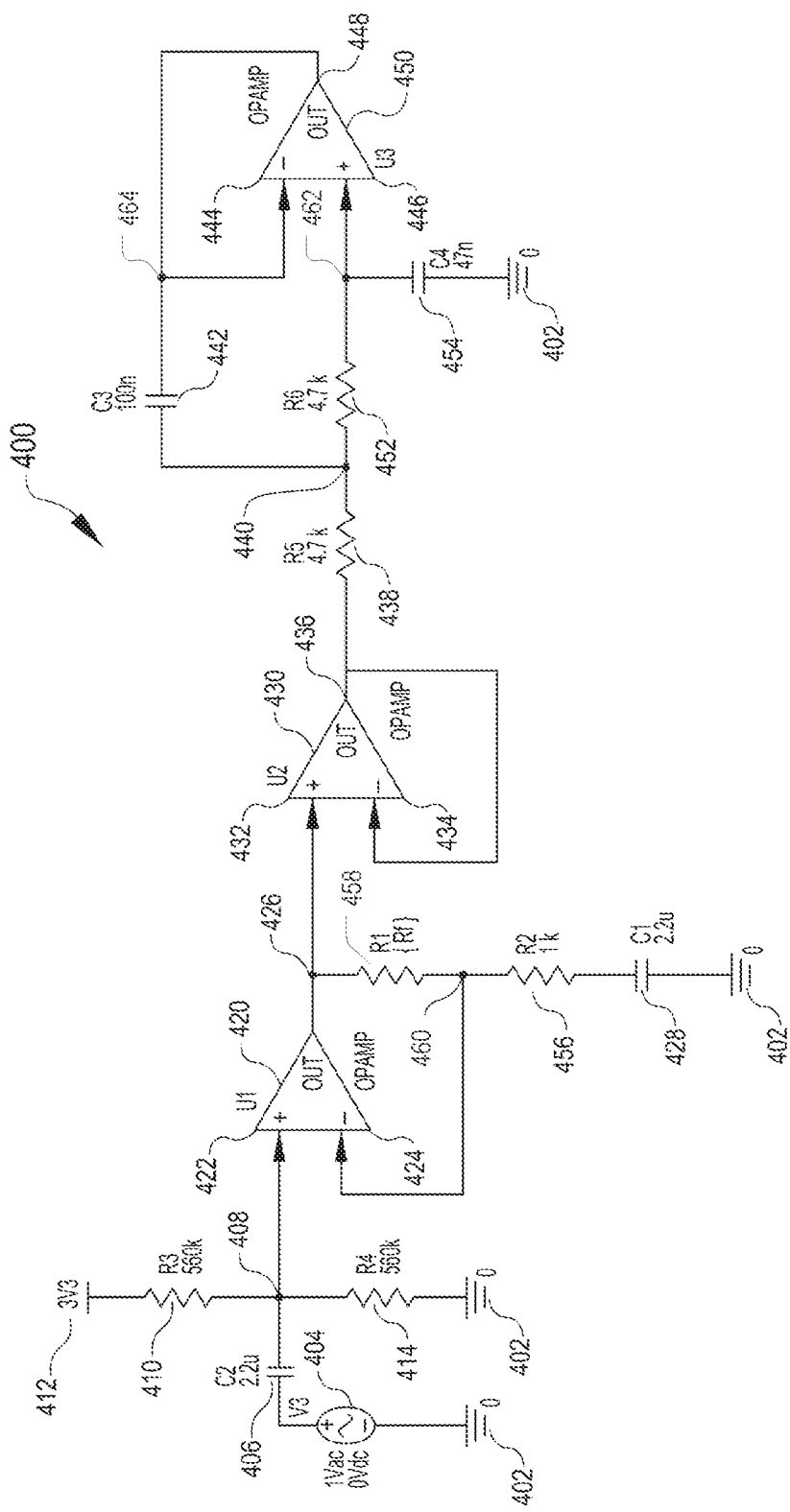
FIG. 4 is an exemplary simplified circuit diagram showing an embodiment of a fetal phonocardiogram signal conditioning circuit, in accordance with embodiments.

FIG. 4 is an exemplary simplified circuit diagram showing an embodiment of a fetal phonocardiogram signal conditioning circuit 400, suitable for use in a fetal phonocardiogram system such as the system 100 shown in FIG. 1, in accordance with embodiments. In some cases, the conditioning circuit 400 can be included in a sensor such as the sensor 112 (shown in FIGS. 2-3) or sensors 112a-d (shown in FIG. 1); but in other cases, the conditioning circuit 400 can be included in the signal conditioner element 120 (FIG. 1). In embodiments, a conditioning circuit such as the circuit 400 is provided for each sensor of the sensor array; but in some cases, a single conditioning circuit could be operably connected with one sensor at a time and switch between the sensors.

The signal conditioning circuit 400 is configured to amplify phonogram signals received from sensors, such as the sensors 112a-d (FIG. 1), by passing a raw signal through three operation amplifiers 420, 430, and 450 in a cascaded configuration. The signal source 404 is connected between ground 402 and a first capacitor 406 for supplying a source for the signal amplification. A first node 408 is also operably connected with the first capacitor 406, and is operably connected between a power source 412 and ground 402 via first and second resistors 410 and 414, respectively. The potential at the first node 408 fluctuates in response to the signal at 404 by way of the first capacitor, and operably connected with the first input terminal 422 of the first operational amplifier 420. The first operational amplifier 420 outputs a voltage at the second node 426.

The second note 426 is operably connected with a first feedback node 460 via a third resistor 458, as well as being operably connected with the first input terminal 432 of the second operational amplifier. The first feedback node 460 is connected with the second input terminal 424 of the first operational amplifier, and connected via a fourth resistor 456 with ground 402 via a second capacitor 428. The effect of the operational amplifier is to amplify the potential of the first node 408 at the second node 426. The second node 426 connects with the first input terminal 432 of the second operational amplifier 430, which outputs a potential at the third node 436 which is operably connected in a feedback loop with the second operational amplifier 430 at the second input terminal 434. The third node 436 is operably connected with a fourth node 440 across a fifth resistor 438. The fourth node 440 is further connected with a fifth node 462 across a sixth resistor 452 and with a sixth node across a third capacitor 442. The fifth node 462 is further connected with the first input terminal 446 of the third operational amplifier 450 and with a fourth capacitor 454 which is connected with ground 402. The output 448 of the third operational amplifier 450 is operably connected with a sixth node 464, which is connected in a feedback loop with the third operational amplifier at the second input 444 of the third operational amplifier, and also connected with the third capacitor 442. An amplified signal can be obtained at the sixth node 464.

The effect of the cascading operational amplifier circuit 400 shown is to increase a signal strength of the input signal without merely adding noise. In some embodiments, other high-gain amplification circuits may be supplied in place of the circuit 400 shown, such as an instrumentation amplifier, feedback-free instrumentation amplifier, chopper-stabilized or zero-drift instrumentation amplifier, or other suitable amplifier circuit.

Figure 5:
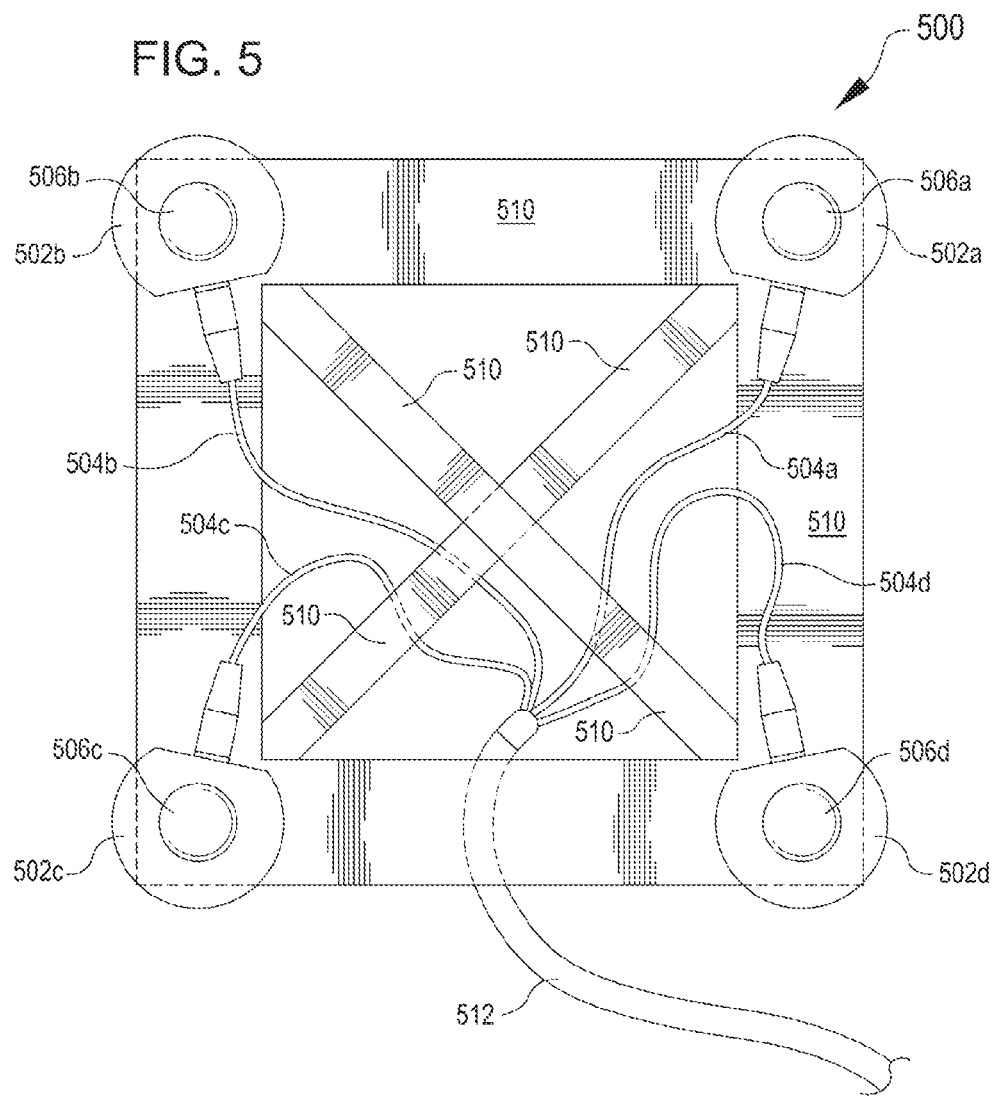
FIG. 5 is perspective view of a fetal phonocardiogram sensor array for use in the system of FIG. 1, in accordance with embodiments.

FIG. 5 is perspective view of an example fetal phonocardiogram sensor array 500 suitable for use in a fetal phonocardiogram system such as the system 100 of FIG. 1, in accordance with embodiments. The array 500 includes four sensors 502a-d arranged in a square configuration and removably attached with a support structure 510. Each of the sensors 502a-d can be configured similarly to the sensor 112 shown in FIGS. 1-3. The array 500 is arranged having a contact side for contacting the patient (shown facing) and a non-contact side that faces away from the patient. The support structure can be a fabric sheet or a web of connected fabric strips, and can be flexible. In some cases, it may be preferable for the support structure 510 to have minimal or no stretch, such that a distance between sensors connected with the support structure 510 can be consistent when the support structure is pulled taut. In some alternative embodiments, the sensors 502a-d can be pivotally connected with a rigid or semi-rigid support structure so as to improve a consistency of the distance between the sensors. A rigid or semi-rigid support structure can be formed of any suitable structural material, such as a plastic like ABS plastic, or a metal such as aluminum. Where a support structure is rigid or semi-rigid, it may also form a curved shape and configured to connect with the sensors at the convex side of the curved shape; so as to accommodate the convex shape of a patient's abdominal region. Also shown are sensor acoustic probes 506a-d, which are configured to come into contact with the skin of a patient, and output leads 504a-d, which combine in an output cable 512 that can carry signals to an signal conditioner element and/or to a processing element (not shown).

Figure 6:
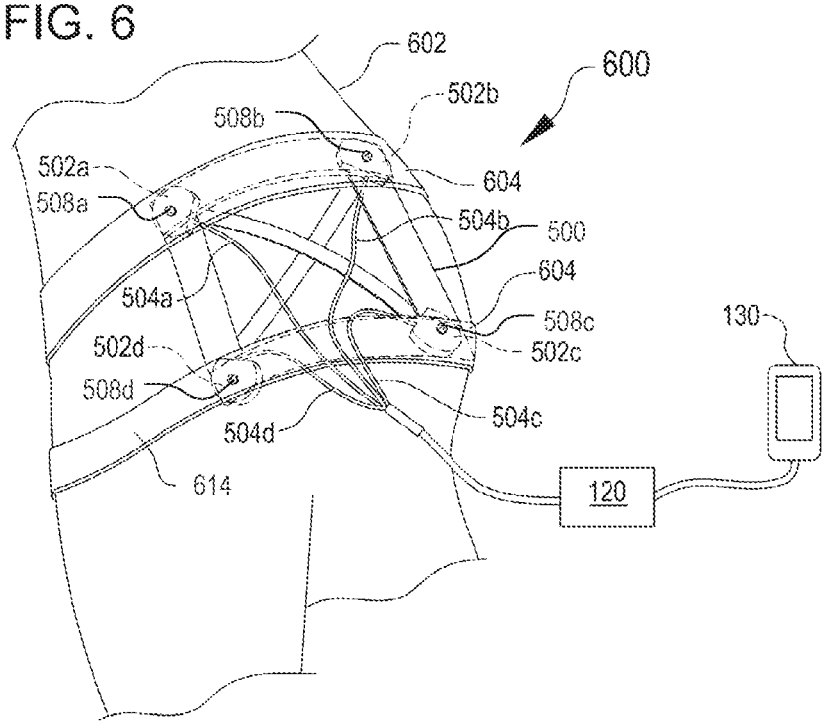
FIG. 6 is a perspective view of a second example of a fetal phonocardiogram system, including the sensor array of FIG. 5 attached to a person, in accordance with embodiments.

FIG. 6 is a perspective view of a fetal phonocardiogram system 600 wherein the sensor array 500 of FIG. 5 is shown attached to a person 602, in accordance with embodiments. In the fetal phonocardiogram system 600, the contact side of the sensor array 500 is connected with the skin of the patient 602, and the non-contact side is facing out. The four sensors 502a-d are arranged in contact with the patient 602 in a square configuration symmetrically disposed around the abdominal region of the patient. Attachment features 508a-d of the sensors 502a-d protrude through openings in the support structure 510, which is stretched taught over the abdomen of the patient 602; and the attachment features 508a-d also protrude through openings in straps 614 which are configured to wrap around the body of the patient 602 and hold the sensor array 500 in contact with the patient. The sensors 502a-d have leads 504a-d which transmit acoustic data from the sensors to the amplifier/buffer element 120, which can process and store acoustic data for further transmission to the processing element 130.

In various alternative embodiments, different arrangements of sensors can be used. For example, a sensor array can have more or less than four sensors. In some cases, sensor array having a centrally disposed sensor in an 'X'-shaped configuration may be provided so as to detect fetal sounds when a fetus is centrally disposed relative to the sensor array. In some cases, a sensor array forming a grid, such as a 3 by 3 grid, may be provided so as to detect fetal sounds when the sounds are not sufficiently strong to be reliably detected by a sensor array using only four sensors. In some cases, a distance between the sensors need not be equal—i.e., the shape of a 2 by 2 grid need not be square, but can also be rectangular, diamond-shaped, 'Y'-shaped, or any other suitable shape that can form a grid. In some cases, three sensors may be disposed in a triangular configuration. In any case, a support structure can be configured to match a desired configuration of the sensors.

Figure 7:
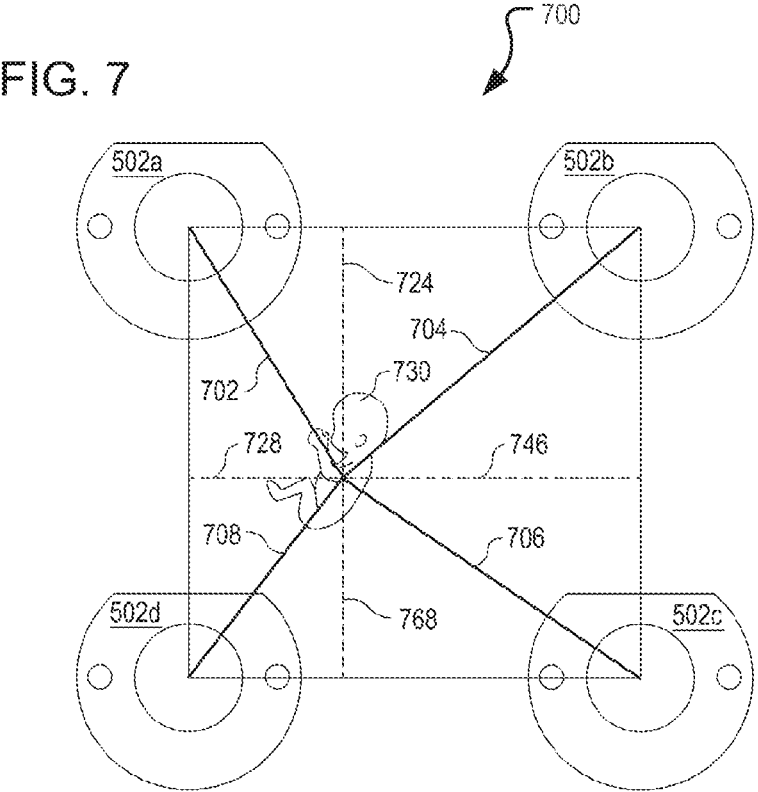
FIG. 7 is a simplified schematic of the fetal phonocardiogram sensor array shown in FIGS. 5 and 6, in relation to an exemplary fetal position, in accordance with embodiments.

FIG. 7 is a simplified schematic of the system 700 including the fetal phonocardiogram sensor array 500 shown in FIGS. 5 and 6, in relation to an exemplary fetal position 730, in accordance with embodiments. The phonocardiogram sensor array 500 including the four sensors 502a-d is placed in an square configuration (e.g., in the support structure 510 shown in FIGS. 5 and 6). The intensity of a fetal heartbeat sound is identified by each sensor, resulting in acoustic intensity values associated with each of the four sensors. The acoustic intensity values can be normalized against a distance between the sensors by the inverse square law, so as to generate distance information associated with each sensor, resulting in the distances 702, 704, 706 and 708. For example, sound intensity is inversely proportional to the square of the distance 'r' from the source.

$$I \propto \frac{1}{r^2}$$

Accordingly, sounds intensities received at multiple sensors arranged in the grid can be used to determine the relative distance of the sound source between pairs of sensors. For example, where the array 500 detects four sound intensities $I_1, I_2, I_3,$ and $I_4$; a position of the fetus based on the array can be determined by solving for associated distances $r_1, r_2, r_3,$ and $r_4$. The intersection of the radiuses $r_1$-$r_4$ is the position of the source of the fetal heartbeat. The distances 702, 704, 706, and 708 can be converted geometrically to vertical or horizontal distances from the reference edges of a grid formed by the array, such as horizontal distance from the left edge 728 or right edge 746, or vertical distance from the top edge 724 or bottom edge 768. In some cases, three of the four sound intensities can be used to detect the position, permitting the fourth sensor of the four sensors to be used for monitoring low-frequency sounds associated with fetal movement.

In specific embodiments, the grid edges can be 10 cm based on distances between openings in the support stricture (not shown). The distances can also be determined or verified via ultrasonography.

Figure 8:
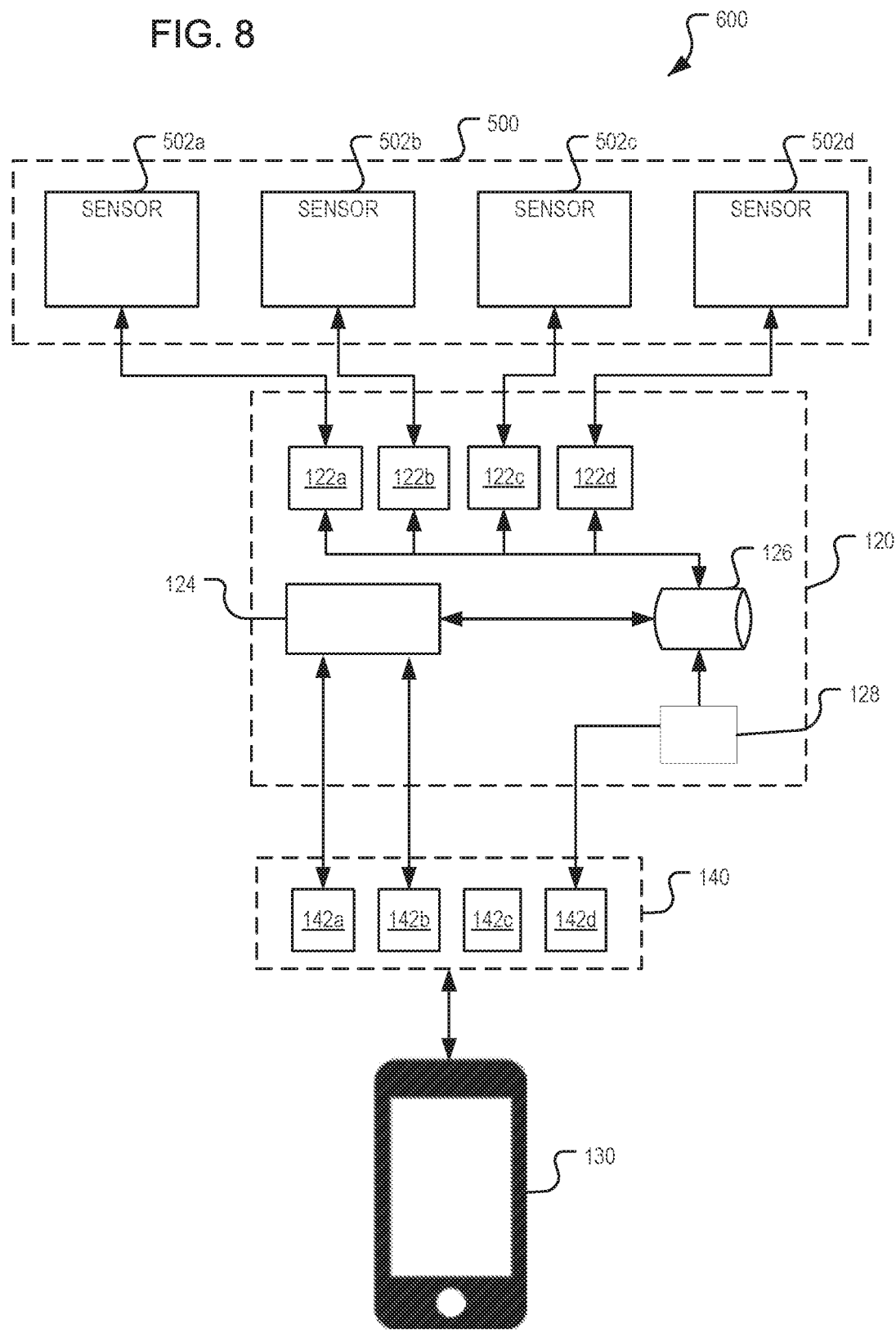
FIG. 8 is a block diagram illustrating an exemplary system for controlling the fetal phonocardiogram system of FIG. 1, in accordance with embodiments.

FIG. 8 is a block diagram illustrating an exemplary system for managing a flow of sensor data in the fetal phonocardiogram system 600 of FIG. 6, in accordance with embodiments. As also shown in FIG. 6, the sensor array 500 is operably connected with an signal conditioning element 120 which is operably connected with a processing element 130, which can be a mobile device as described above in reference to FIG. 1. Each of the sensors 502a, 502b, 502c, and 502d (collectively 502) can communicate acoustic data with signal processing modules 122a, 122b, 122c, and 122d, (collectively 122) respectively in the signal conditioning element 120. The signal processing modules 122 can include signal conditioning circuits, such as the signal conditioning circuit 400 shown in FIG. 4; and may also include switches operable to control the receipt and/or output of signals at each processing module. The signal processing modules 122 feed amplified sensor data to the buffer 126 for at least temporary storage. The buffer 126 may in some cases collect data continuously from all of the conditioning circuits; or in some cases, the buffer 126 can be controlled by a data I/O module 124 to selectively receive data from one signal processing module at a time. The data I/O module 124 can also communicate with the buffer 126 to cause the buffer to selectively output data from one signal processing module to the processing element 130.

In some specific embodiments, the processing element 130 can be a mobile device, such as a mobile phone, tablet computer, laptop computer, or other suitable computing device. Furthermore, in some cases, the processing element 130 can be configured to receive data via a standard audio port having, for example, two stereo leads 142a; 142b, a ground lead 142c, and a microphone lead 142d. The processing element, which can contain a processor and memory containing executable instructions for at least managing acoustic data, can use two of said leads in the audio port such as the two stereo leads 142a, 142b to issue binary instructions to the data I/O module 124 of the signal conditioner element 120 in order to instruct the buffer 126 to relay an acoustic signal via a third lead in the audio port such as the microphone lead 142d. The processing element 130 can, in some cases, selectively receive one acoustic signal at a time in real-time; i.e., by causing the data I/O module 124 to select a signal source to listen to; or the processing element 130 can capture stored acoustic signals from multiple sensors that have been acquired at the buffer 126 over a period of time. In some cases, the signal conditioner element 120 can also include a modulator for incorporating the acoustic signals into a carrier wave. In some specific embodiments, the carrier wave has a frequency of 2 kHz.

Figure 9:
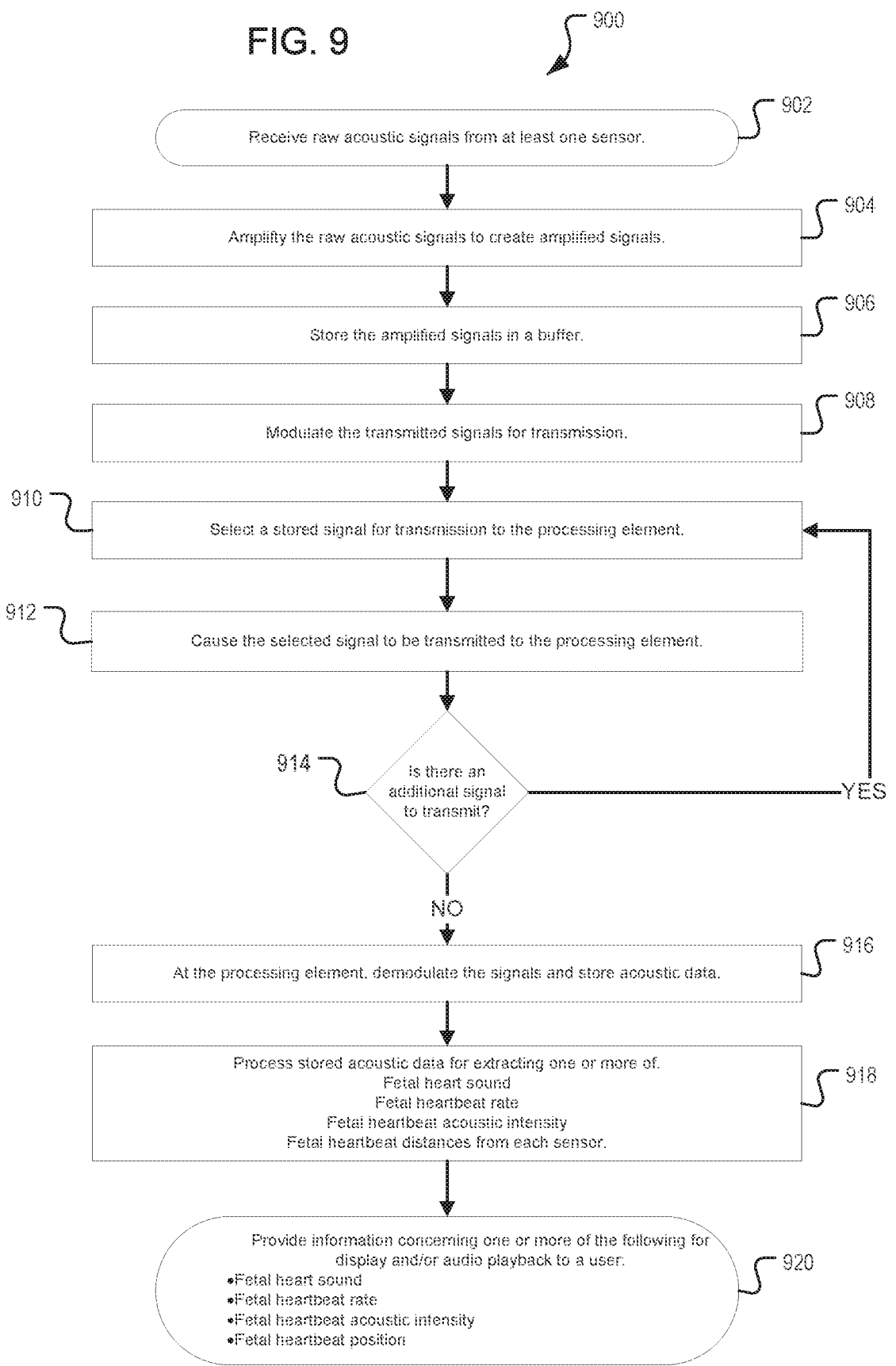
FIG. 9 is an first exemplary process flow chart for using the system of FIG. 8, in accordance with embodiments.

FIG. 9 is an exemplary process flow chart of a first process 900 for controlling the system 600 of FIGS. 6 and 8, in accordance with embodiments. In the process 900, the system receives a raw acoustic signal at least one sensor. (902) The raw acoustic signal is conditioned and/or amplified to create an amplified signal. (904) The amplified signal can be stored at a buffer (906) or in some cases can be transmitted directly to a processing element. In some cases, the amplified signal may be modulated for transmission, i.e., in order to accommodate an input/output path (such as a conventional audio input to a portable device) that is already configured to filter frequencies. (908) The system can select a stored signal for transmission to the processing element (910) and then cause the buffer to transmit the stored signal to the processing element. (912) In some cases, an amplified signal may be continuously transmitted from one or more sensors, in which case a buffer at the processing element may instead be configured to select a channel corresponding to a sensor in order to receive the continuously transmitted signal. The system determines whether there is an additional signal to transmit (or to receive) (914), and, if so, the system can select the new signal and/or channel and transmit the new signal and/or channel to the processing element. (910) In some cases, the system can repetitively sample each channel of multiple channels containing signals according to a predetermined period of time, according to a user input, or other suitable event. At the processing element, the system can demodulate the received signals and store acoustic data associated with the received signals. (916) The processing element can then process the acoustic data for extracting information related to the fetal heartbeat. In some cases, said acoustic data can include any or all of, or any combination of, the fetal heart sound, the fetal heartbeat rate, the fetal heartbeat acoustic intensity, or the distance between the fetal heartbeat and each sensor. (918) In some cases, the system may capture acoustic data indicating fetal movement, which can also be processed and extracted. Then, the system can provide information to a user concerning one or more of the above attributes. (920) For example, the system may play back an audio file based on the fetal heartbeat sound for a user, may provide a graph showing the fetal heartbeat rate, acceleration, or strength; and may provide indicators of fetal heartbeat location based on the location of a sensor array used to obtain the fetal heartbeat data. Aspects of the process 900 may be performed by a system similar to the systems 100 discussed in FIG. 1 or the system 600 discussed in FIGS. 6 and 8.

Figure 10:
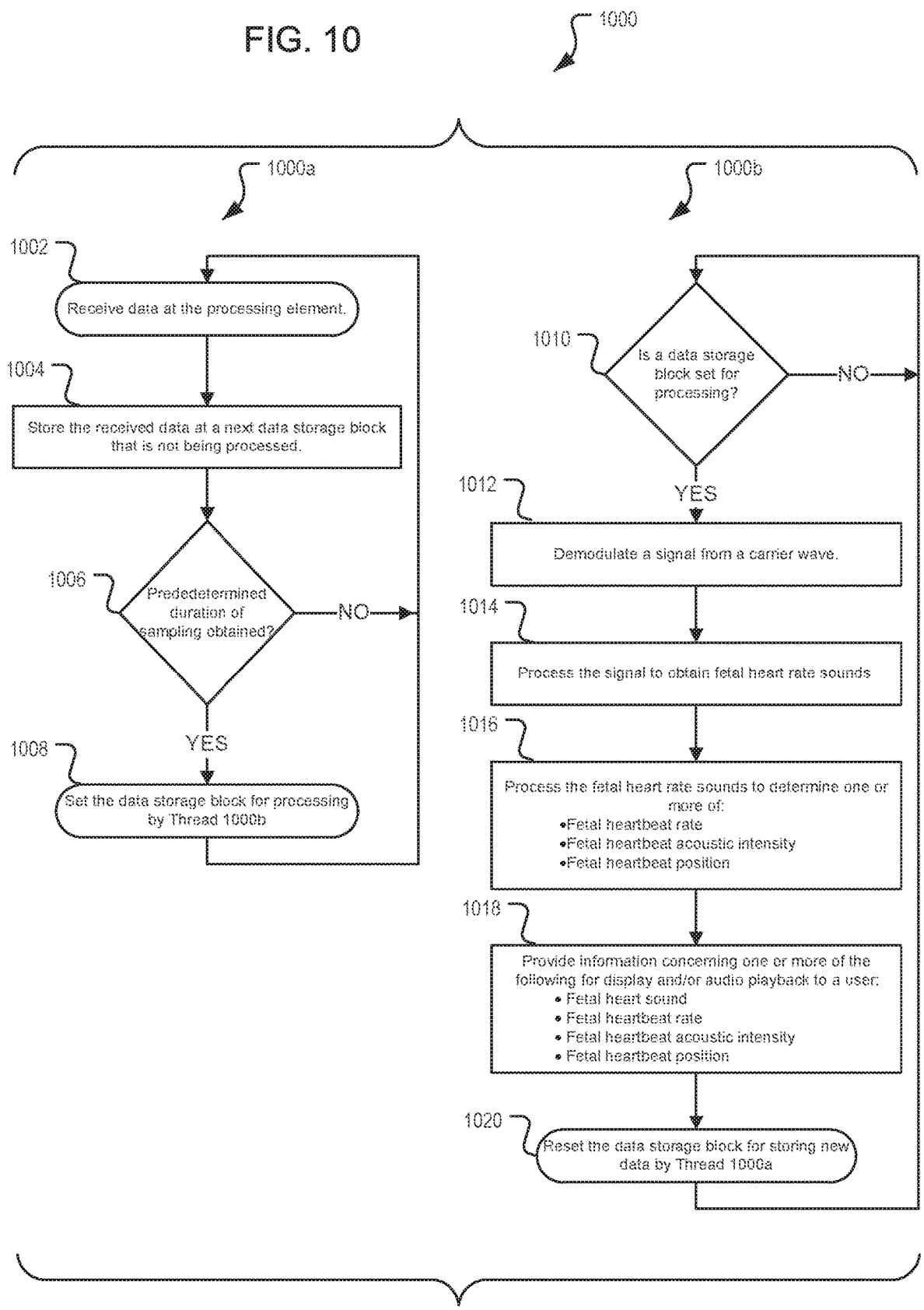
FIG. 10 is a second exemplary process flow chart for using the system of FIG. 8, in accordance with embodiments.

FIG. 10 is an exemplary process flow chart of a second process 1000 for controlling the system 600 of FIGS. 6 and 8, and specifically for controlling a flow of data between the sensors and the processing element, in accordance with embodiments. In the process 1000, a first thread 1000a and a second thread 1000b can operate in parallel. At the first thread 1000a, a processing element receives a flow of acoustic data. (1002) The processing element determines that a storage block, which may be a buffer or any other suitable memory device for storing acoustic data, is not currently being used for storing new acoustic data, and begins to store the acoustic data thereat. (1004) The system checks whether the flow of data has been sampled for a predetermined duration. (1006) If it has not been sampled for the entire duration, the system continues to receive the data flow. If it has been sampled for the entire duration, the system will stop storing new data in the originally selected storage block and begin processing the data according to the second thread 1000b. Concomitantly, the first thread 1000a will begin sampling a flow of acoustic data from a different source. In some embodiments, the sampling duration may be on the order of seconds; and in a specific embodiment, the sampling duration may be approximately 2 seconds.

At the second thread, 1000b, the processing element determines that a data storage block has been set by the first thread 1000a for processing. (1010) The processing element can demodulate the stored signal from a carrier wave if the signal has been modulated in said carrier wave (1012). The demodulated signal can then be processed to obtain fetal heart rate sounds. (1014). The fetal heart rate sounds can be used to determine, for example, a fetal heartbeat rate (or change in rate), or a fetal heartbeat acoustic intensity (which can also be used to determine a fetal heartbeat position). (1018) Aspects of the process 1000 may be performed by a system similar to the systems 100 discussed in FIG. 1 or the system 600 discussed in FIGS. 6 and 8.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A fetal monitoring system, comprising:
a sensor array comprising:
four sensors configured to be coupled with a patient in a rectangular array around an abdomen of the patient, wherein each of the four sensors is configured to convert acoustic waves into a respective acoustic signal; and
a support structure configured to attach with the four sensors to maintain an array spacing of the rectangular array;
a signal conditioning assembly comprising four signal processing modules, a data input/output module, a buffer, and a signal conditioning assembly communication port; wherein each of the four signal processing modules is configured to receive the respective acoustic signal from a respective one of the four sensors, amplify the acoustic signal to generate an amplified acoustic signal, and output the amplified acoustic signal to the buffer; and wherein the data input/output module is operatively coupled with the buffer and configured to receive instructions via the signal conditioning assembly communication port that cause the data input/output module to issue instructions to the buffer to output one or more of the amplified acoustic signals via the signal conditioning assembly communication port for processing; and
a mobile computing device comprising a mobile computing device communication port that can be selectively operatively coupled with the signal conditioning assembly communication port, at least one processor and memory containing executable instructions that, when executed by the at least one processor, cause the at least one processor to:
transmit the instructions via the mobile computing device communication port and the signal conditioning assembly communication port to the data input/output module that cause the data input/output module to issue instructions to the buffer to output the amplified acoustic signals to the mobile computing device;
process the amplified acoustic signals to generate a first mixed signal;
generate a first mixed filtered signal by processing the first mixed signal using low-pass filtering and high-pass filtering to remove frequencies not associated with fetal heartbeat and fetal movement;
generate fetal heartbeat information by processing the first mixed filtered signal to remove a maternal heartbeat signal from the first mixed filtered signal; and
output at least the fetal heartbeat information for presentation to a user.

2. The fetal monitoring system of claim 1, wherein each sensor of the four sensors is a phonocardiogram sensor that further comprises an acoustic transducer, a casing and an acoustic chamber that protrudes from the casing.

3. The fetal monitoring system of claim 2, wherein:
one sensor of the four sensors is a movement sensor configured to convert acoustic waves in a frequency range associated with fetal movement into a fetal movement acoustic signal;
one of the four signal processing modules is configured to amplify the fetal movement acoustic signal to generate an amplified fetal movement acoustic signal;
the executable instructions, when executed by the at least one processor, further cause the at least one processor to:
receive the amplified fetal movement acoustic signal from the signal conditioning assembly;
process the amplified fetal movement acoustic signal to detect fetal movement; and
generate an additional output communicating fetal movement information based on the detection of the fetal movement for receipt by a user.

4. The fetal monitoring system of claim 2, wherein the executable instructions, when executed by the at least one processor, further cause the at least one processor to:
determine, based on the fetal heartbeat information, a location of a fetus relative to the rectangular array; and
output location information indicative of the location of the fetus.

5. The fetal monitoring system of claim 2, wherein each sensor of the four sensors comprises a piezoelectric disk sensor.

6. The fetal monitoring system of claim 1, wherein:
each of the signal conditioning assembly communication port and the mobile computing device communication port comprises a respective audio port comprising a respective two stereo leads, a respective ground lead, and a respective microphone lead;
the instructions are transmitted to the data input/output module via both of the respective two stereo leads; and
the amplified acoustic signals are output to the mobile computing device via the respective microphone leads.

7. The fetal monitoring system of claim 6, wherein the executable instructions are further configured to cause the at least one processor to separately:
receive a first of the amplified acoustic signals from the buffer of the signal conditioning assembly;
store the first of the amplified acoustic signals in the memory;
receive a second of the amplified acoustic signals from the buffer of the signal conditioning assembly;
store the second of the amplified acoustic signals in the memory;
receive a third of the amplified acoustic signals from the buffer of the signal conditioning assembly;
store the third of the amplified acoustic signals in the memory;
receive a fourth of the amplified acoustic signals from the buffer of the signal conditioning assembly; and store the fourth of the amplified acoustic signals in the memory.

8. The fetal monitoring system of claim 1, wherein the support structure is further configured to retain each of the four sensors at fixed distances from one another.

9. The fetal monitoring system of claim 1, wherein each of the four sensors comprises a respective positive surface feature configured to removably connect with one of a plurality of corresponding negative features in the support structure.

10. The fetal monitoring system of claim 1, further comprising a strap configured to pass around a body of a patient and removably attach around the patient, wherein the strap comprises negative features configured for attaching with the four sensors so as to press the four sensors against the body of the patient.

11. The fetal monitoring system of claim 1, wherein the mobile computing device comprises a mobile phone, a tablet computer, or a laptop computer.

12. The fetal monitoring system of claim 1, wherein the buffer stores at least one of the amplified acoustic signals digitally.

\* \* \* \* \*

UNITED STATES PATENT AND TRADEMARK OFFICE
CERTIFICATE OF CORRECTION

PATENT NO. : 11,185,275 B2
APPLICATION NO. : 15/756822
DATED : November 30, 2021
INVENTOR(S) : Ahsan Khandoker It is certified that error appears in the above-identified patent and that said Letters Patent is hereby corrected as shown below:

On the Title Page

Column 1, item (73), delete "Khalifa Univeristy" and insert --Khalifa University--

Signed and Sealed this
Eleventh Day of October, 2022

Katherine Kelly Vidal
*Director of the United States Patent and Trademark Office*